(12) United States Patent
Ise

(10) Patent No.: US 6,764,777 B2
(45) Date of Patent: Jul. 20, 2004

(54) SULFUR-CONTAINING COMPOUND AND LIGHT-EMITTING DEVICE USING SAME

(75) Inventor: Toshihiro Ise, Suwa (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 0 days.

(21) Appl. No.: 10/366,666

(22) Filed: Feb. 14, 2003

(65) Prior Publication Data

US 2003/0180575 A1 Sep. 25, 2003

(30) Foreign Application Priority Data

Feb. 21, 2002 (JP) ........................................ 2002-045226

(51) Int. Cl.$^7$ .......................... B32B 19/00; B32B 9/00; C07D 331/02; C07D 335/00; C07D 327/06; C07D 327/10; H01J 63/04
(52) U.S. Cl. .......................... 428/690; 428/917; 549/1; 549/13; 549/14; 549/15; 549/29; 549/30; 549/31; 549/35; 313/504; 313/506
(58) Field of Search ................................. 549/1, 29, 30, 549/31, 35, 13, 14, 15; 428/690, 917; 313/504, 506

(56) References Cited

U.S. PATENT DOCUMENTS 6,652,997 B2 * 11/2003 Suzuki et al. ............... 428/690

FOREIGN PATENT DOCUMENTS

JP 11-111462 4/1999

OTHER PUBLICATIONS

Pure & Applin. Chem., vol. 54, No. 5, pp. 927–938, 1982.

* cited by examiner

Primary Examiner—Camie S. Thompson
(74) Attorney, Agent, or Firm—Sughrue Mion, PLLC

(57) ABSTRACT

The compound represented by the general formula (I):

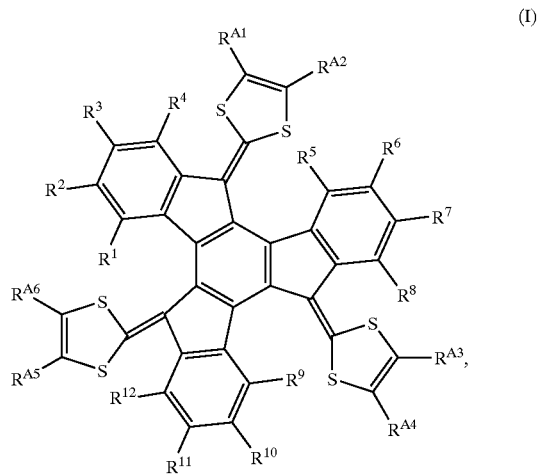

wherein each of $R^1$ to $R^{12}$ and $R^{A1}$ to $R^{A6}$ represents a hydrogen atom or a substituent group, and adjacent groups of $R^1$ to $R^{11}$ and $R^{A1}$ to $R^{A6}$ may be bonded to each other to form a ring. The light-emitting device of the present invention comprises a pair of electrodes and one or more organic layers disposed therebetween, at least one of the organic layers comprising the above compound.

20 Claims, No Drawings

SULFUR-CONTAINING COMPOUND AND LIGHT-EMITTING DEVICE USING SAME

FIELD OF THE INVENTION

The present invention relates to a novel, disc-like, sulfur-containing compound usable as functional materials such as light-emitting device materials, discotic liquid crystal materials, organic conductive materials (electrically conductive charge-transporting complexes, electrically conductive radical salts, etc.), organic ferromagnetic materials, etc., and a light-emitting device using the compound.

BACKGROUND OF THE INVENTION

Organic conductive materials have been researched and developed actively in recent years because they are light in weight and excellent in corrosion resistance, etc. unlike metal materials such as gold, silver and copper, and electrically conductive metal oxide materials such as ITO. Known as high-conductive, organic materials are most of charge-transporting complexes and radical cation salts, which are derived from electron-donating compounds having a 1,3-dithiol ring with a typical example of tetrathiafulvalene (TTF), and various electron-accepting compounds or inorganic anions.

It is known that discotic liquid crystals can be used as charge-transporting materials in various devices. For example, Adam, et al. reported that triphenylene-based, discotic liquid crystalline phase exhibited mobility of $10^{-3}$ to $10^{-2}$ cm$^2$/Vs (Nature, Vol. 371, Page 141). Also disclosed are examples of using the discotic liquid crystals for such devices as organic electroluminescence (EL) devices.

Organic ferromagnetic materials have been actively researched for use in place of metal magnets such as iron-based magnets, etc. Reported by Breslow, R. is that in a charge-transporting complex derived from a dication of donor molecule and a dianion of acceptor molecule, one molecule is stably in a triplet ground state with parallel spins to provide ferromagnetic interaction (Pure and Applied Chemistry, Vol. 54, page 927, 1982). According to the group theory, a molecule with symmetry of $C_3$ or more or $D_{2d}$ has a degenerate molecular orbital and can be converted into the triplet ground state. Therefore, various high-symmetry molecules have been developed to synthesize ferromagnetic substances.

However, the organic conductive materials, the charge-transporting liquid crystals and the organic ferromagnetic materials mentioned above fail to show sufficient performance for industrial use.

Research and development are recently active worldwide to provide various light-emitting devices. Among others, organic electroluminescence (EL) devices are advantageous in that they are extremely thin, light in weight, rapid in response, wide in viewing angle, low in driving voltage, etc., thereby attracting much attention as a promising light-emitting device. Although various materials have been evaluated as components for the light-emitting devices to develop highly efficient devices with external quantum efficiency of more than 10%, they are still insufficient in durability and need a high driving voltage.

JP 11-111462 A discloses a light-emitting device comprising a compound with a dithiol ring, but it is different in structure from the compound of the present invention.

OBJECTS OF THE INVENTION

Accordingly, an object of the present invention is to provide a novel, disc-like, sulfur-containing compound having charge transportability and electron-donating properties.

Another object of the present invention is to provide a light-emitting device excellent in durability, which can be driven at a low driving voltage.

SUMMARY OF THE INVENTION

The compound according to the present invention has a chemical structure represented by the general formula (I):

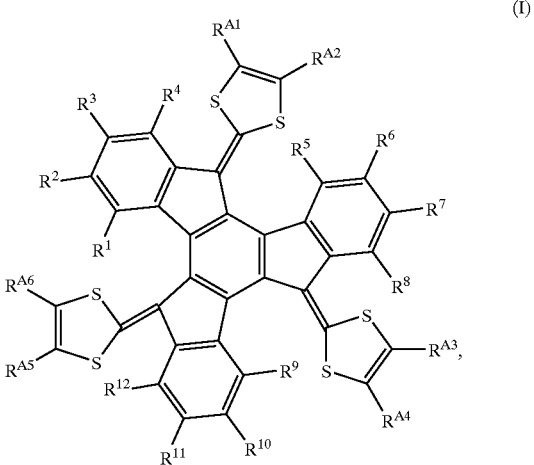

(I)

wherein each of $R^1$ to $R^{12}$ and $R^{A1}$ to $R^{A6}$ represents a hydrogen atom or a substituent group, and adjacent groups of $R^1$ to $R^{12}$ and $R^{A1}$ to $R^{A6}$ may be bonded to each other to form a ring.

The compound of the present invention is preferably has a chemical structure represented by the general formula (II):

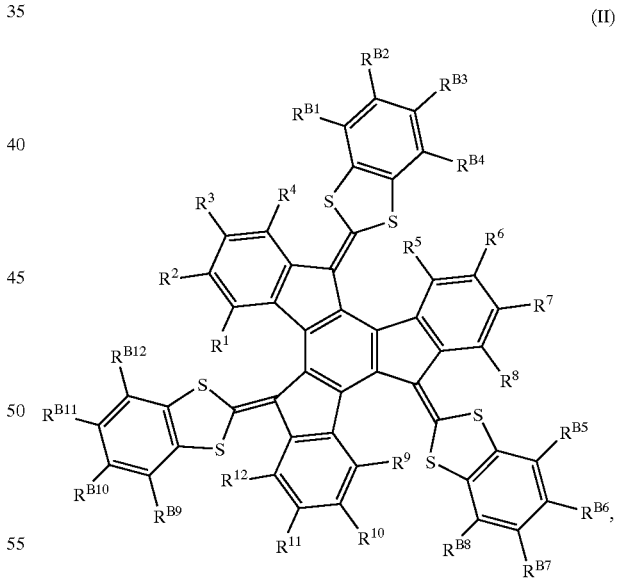

(II)

wherein each of $R^1$ to $R^{12}$ and $R^{B1}$ to $R^{B12}$ represents a hydrogen atom or a substituent group.

The light-emitting device according to the present invention comprises a pair of electrodes and one or more organic layers comprising a light-emitting layer disposed therebetween, at least one of the organic layers comprising at least one compound represented by the general formula (I) or (II).

In the light-emitting device of the present invention, at least one of the organic layers is preferably a layer having at least one compound represented by the general formula (I) or (II) dispersed in a polymer.

Each of $R^1$, $R^4$, $R^5$, $R^8$, $R^9$ and $R^{12}$ is preferably a hydrogen atom or an alkyl group, more preferably a hydrogen atom. Each of $R^2$, $R^3$, $R^6$, $R^7$, $R^{10}$ and $R^{11}$ is preferably a hydrogen atom, an alkyl group, an alkylthio group, an alkyloxy group, a cyano group, alkyloxy group or a halogen atom, more preferably a hydrogen atom, an alkyl group or an alkylthio group. Each of $R^{A1}$ to $R^{A6}$ is preferably a hydrogen atom, alkyl group, alkyloxy group, alkylthio group, a cyano group or halogen atoms, more preferably a hydrogen atom, alkyl group or alkylthio group. Each of $R^{B1}$ to $R^{B12}$ is preferably a hydrogen atom or an alkyl group.

At least one organic layer in the light-emitting device preferably further comprises a polymer. The above at least one organic layer is preferably a hole-injecting layer or a hole-transporting layer.

The amount of the compound represented by the formula (I) or (II) in a hole-injecting layer or a hole-transporting layer is preferably from 10 to 100% by weight, more preferably from 50 to 100% by weight. The amount of the compound represented by the formula (I) or (II) in the other layers except a hole-injecting layer or a hole-transporting layer is preferably from 5 to 90% by weight, more preferably from 5 to 50% by weight.

DETAILED DESCRIPTION OF THE PREFERRED EMBODIMENTS

[1] Sulfur-containing Compound

In the general formula (I), each of $R^1$ to $R^{12}$ and $R^{A1}$ to $R^{A6}$ represents a hydrogen atom or a substituent group, and may be the same or different. Examples of the substituent groups represented by $R^1$ to $R^{12}$ and $R^{A1}$ to $R^{A6}$ include halogen atoms, alkyl groups, alkenyl groups, alkynyl groups, aryl groups, heterocyclic groups, a cyano group, a hydroxyl group, a nitro group, a carboxyl group, alkoxy groups, aryloxy groups, silyloxy groups, heterocyclic oxy groups, acyloxy groups, carbamoyloxy groups, alkoxycarbonyloxy groups, aryloxycarbonyloxy groups, an amino group, acylamino groups, aminocarbonylamino groups, alkoxycarbonylamino groups, aryloxycarbonylamino groups, sulfamoylamino groups, alkylsulfonylamino groups, arylsulfonylamino groups, mercapto groups, alkylthio groups, arylthio groups, heterocyclic thio groups, sulfamoyl groups, a sulfo group, alkylsulfinyl groups, arylsulfinyl groups, alkylsulfonyl groups, arylsulfonyl groups, acyl groups, aryloxycarbonyl groups, alkoxycarbonyl groups, a carbamoyl group, arylazo groups, heterocyclic azo groups, imide groups, a phosphino group, a phosphinyl group, a phosphinyloxy group, a phosphinylamino group and silyl groups. The adjacent groups of $R^1$ to $R^{12}$ and $R^{A1}$ to $R^{A6}$ may be bonded to each other to form a ring, if possible.

Each of $R^1$, $R^4$, $R^5$, $R^8$, $R^9$ and $R^{12}$ is preferably a hydrogen atom or an alkyl group and particularly a hydrogen atom. The above alkyl group is a group preferably with 1 to 3 carbon atoms, more preferably with 1 or 2 carbon atoms, particularly a methyl group.

In a case where the compound represented by the general formula (I) is used as a liquid crystal material, preferred examples of $R^2$, $R^3$, $R^6$, $R^7$, $R^{10}$ and $R^{11}$ include alkyl groups, the number of carbon atoms thereof being preferably 2 to 30, more preferably 2 to 20, which may be unsubstituted alkyl groups such as an ethyl group, a propyl group, a butyl group, a pentyl group, a hexyl group, a heptyl group, an octyl group, a nonyl group, a decyl group, an undecyl group, a dodecyl group and an eicosyl group; or substituted alkyl groups such as a 4-methoxybutyl group and a 6-methoxyhexyl group; alkyloxy groups, the number of carbon atoms thereof being preferably 2 to 30, more preferably 2 to 20, which may be unsubstituted alkyloxy groups such as an ethyloxy group, a propyloxy group, a butyloxy group, a pentyloxy group, a hexyloxy group, a heptyloxy group, an octyloxy group, a nonyloxy group, an undecyloxy group and a dodecyloxy group; or substituted alkyloxy groups such as a 4-methoxybutyloxy group and a 6-methoxyhexyloxy group; acyloxy groups, the number of carbon atoms thereof being preferably 3 to 30, more preferably 3 to 20, which may be unsubstituted acyloxy groups such as an acetoxy group, a propionyloxy group, a butyryloxy group, a valeryloxy group, a hexanoyloxy group, a heptanoyloxy group, an octanoyloxy group, a nonanoyloxy group, an undecanoyloxy group and a dodecanoyloxy group; or substituted acyloxy groups such as a 4-methoxybutyryloxy group and a 6-methoxyhexanoyloxy group; alkoxycarbonyl groups, the number of carbon atoms thereof being preferably 3 to 30, more preferably 3 to 20, which may be unsubstituted alkoxycarbonyl groups such as an ethoxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a nonyloxycarbonyl group, an undecyloxycarbonyl group and a dodecyloxycarbonyl group; or substituted alkoxycarbonyl groups such as a 4-methoxybutyloxycarbonyl group and a 6-methoxyhexyloxycarbonyl group; benzoyloxy groups; and cinnamoyloxy groups. Each of the benzoyloxy groups and the cinnamoyloxy groups may have, at a para position, a substituent group such as an alkyloxy group, an alkyl group, an alkoxycarbonyl group, an acyloxy group, a halogen atom, etc, preferably an alkyloxy group, which may be the same as the above-mentioned alkyloxy group of $R^2$, $R^3$, $R^6$, $R^7$, $R^{10}$ and $R^{11}$. Each of $R^2$, $R^3$, $R^6$, $R^7$, $R^{10}$ and $R^{11}$ is more preferably an alkyl group or an alkyloxy group, most preferably an alkyloxy group.

In a case where the compound represented by the general formula (I) is used for other applications than the liquid crystal material, preferred examples of $R^2$, $R^3$, $R^6$, $R^7$, $R^{10}$ and $R^{11}$ include a hydrogen atom; alkyl groups, the number of carbon atoms thereof being preferably 1 to 30, more preferably 1 to 20, further preferably 1 to 10, particularly 1 to 5, such as a methyl group, an ethyl group and a propyl group; alkoxy groups, the number of carbon atoms thereof being preferably 1 to 30, more preferably 1 to 20, further preferably 1 to 10, particularly 1 to 5, such as a methoxy group, an ethoxy group and an ethylenedioxy group formed by $R^2$ and $R^3$, $R^6$ and $R^7$, or $R^{10}$ and $R^{11}$; alkylthio groups, the number of carbon atoms thereof being preferably 1 to 30, more preferably 1 to 20, further preferably 1 to 10, particularly 1 to 5, such as a methylthio group, an ethylthio group, and a methylenedithio group, an ethylenedithio group and a propylenedithio group formed by $R^2$ and $R^3$, $R^6$ and $R^7$, or $R^{10}$ and $R^{11}$; aryl groups, the number of carbon atoms thereof being preferably 6 to 30, more preferably 6 to 20, further preferably 6 to 10, such as a phenyl group, a naphthyl group and an azulenyl group; heterocyclic groups, the number of carbon atoms thereof being preferably 2 to 30, more preferably 3 to 20, further preferably 3 to 10, which may have such a heterocycle as a thiophene ring, a furan ring, a pyrrole ring, a selenophene ring, a tellurophene ring, a pyridine ring, a pyridazine ring, a pyrimidine ring, a pyrazine ring, a pyrazole ring, an oxazole ring, a thiazole ring, an isoxazole ring, an isothiazole ring, an imidazole ring, a triazine ring, a pyrane ring, a piperazine ring, a pyrroline ring, a pyrrolidine ring, an imidazoline ring, an imidazolidine ring, a pyrazoline ring, a pyrazolidine ring, a furazan ring, a morpholine ring, an indole ring, an indoline ring, an indazole ring, a chromene ring, a chroman ring, an isochroman ring, a quinoline ring, an isoquinoline ring, a cinnoline ring, a phthalazine ring, a quinazoline ring, a quinoxaline ring, a naphthyridine ring, a purine ring, a pteridine ring, an indolizine ring, a carbazole ring, an acridine ring, a phenazine ring, a phenanthridine ring, a phenanthroline ring, a xanthene ring, a phenoxazine ring, a thianthrene ring and a quinuclidine ring, the heterocycle being preferably a thiophene ring, a furan ring, a pyrrole ring or a pyridine ring, more preferably a thiophene ring or a pyridine ring, particularly a thiophene ring; a cyano group; a mercapto group; a hydroxyl group; and halogen atoms such as a fluorine atom, a chlorine atom, a bromine atom and an iodine atom. Each of $R^2, R^3, R^6, R^7, R^{10}$ and $R^{11}$ is more preferably a hydrogen atom, an alkyl group, an alkylthio group, an alkyloxy group, a cyano group or a halogen atom, further preferably a hydrogen atom, an alkyl group, an alkylthio group or a halogen atom, most preferably a hydrogen atom, an alkyl group or an alkylthio group, particularly a hydrogen atom.

Preferred examples of $R^{A1}$ to $R^{A6}$ include a hydrogen atom; a benzene ring formed by $R^{A1}$ and $R^{A2}$, $R^{A3}$ and $R^{A4}$, or $R^{A5}$ and $R^{A6}$ with a dithiol ring; alkyl groups, the number of carbon atoms thereof being preferably 1 to 30, more preferably 1 to 20, further preferably 1 to 10, particularly 1 to 5, such as a methyl group, an ethyl group and a propyl group; alkoxy groups, the number of carbon atoms thereof being preferably 1 to 30, more preferably 1 to 20, further preferably 1 to 10, particularly 1 to 5, such as a methoxy group, an ethoxy group and an ethylenedioxy group formed by $R^{A1}$ and $R^{A2}$, $R^{A3}$ and $R^{A4}$, or $R^{A5}$ and $R^{A6}$; alkylthio groups, the number of carbon atoms thereof being preferably 1 to 30, more preferably 1 to 20, further preferably 1 to 10, particularly 1 to 5, such as a methylthio group, an ethylthio group, and a methylenedithio group, an ethylenedithio group and a propylenedithio group formed by $R^{A1}$ and $R^{A2}$, $R^{A3}$ and $R^{A4}$, or $R^{A5}$ and $R^{A6}$; aryl groups, the number of carbon atoms thereof being preferably 6 to 30, more preferably 6 to 20, further preferably 6 to 10, such as a phenyl group and a naphthyl group; heterocyclic groups, the number of carbon atoms thereof being preferably 2 to 30, more preferably 3 to 20, further preferably 3 to 10, which may have such a heterocycle as a thiophene ring, a furan ring, a pyrrole ring, a selenophene ring, a tellurophene ring, a pyridine ring, a pyridazine ring, a pyrimidine ring, a pyrazine ring, a pyrazole ring, an oxazole ring, a thiazole ring, an isoxazole ring, an isothiazole ring, an imidazole ring, a triazine ring, a pyrane ring, a piperazine ring, a pyrroline ring, a pyrrolidine ring, an imidazoline ring, an imidazolidine ring, a pyrazoline ring, a pyrazolidine ring, a furazan ring, a morpholine ring, an indole ring, an indoline ring, an indazole ring, a chromene ring, a chroman ring, an isochroman ring, a quinoline ring, an isoquinoline ring, a cinnoline ring, a phthalazine ring, a quinazoline ring, a quinoxaline ring, a naphthyridine ring, a purine ring, a pteridine ring, an indolizine ring, a carbazole ring, an acridine ring, a phenazine ring, a phenanthridine ring, a phenanthroline ring, a xanthene ring, a phenoxazine ring, a thianthrene ring and a quinuclidine ring, the heterocycle being preferably a thiophene ring, a furan ring, a pyrrole ring or a pyridine ring, more preferably a thiophene ring or a pyridine ring, particularly a thiophene ring; a cyano group; a mercapto group; a hydroxyl group; halogen atoms such as a fluorine atom, a chlorine atom, a bromine atom and an iodine atom; a carboxyl group; and carbonyloxy groups, the number of carbon atoms thereof being preferably 2 to 30, more preferably 2 to 20, further preferably 2 to 10, such as a methoxycarbonyl group and an ethoxycarbonyl group. More preferred among them are a hydrogen atom, a benzene ring formed by $R^{A1}$ and $R^{A2}$ and $R^{A4}$, or $R^{A5}$ and $R^{A6}$, alkyl groups, alkyloxy groups, alkylthio groups, a cyano group and halogen atoms. Furthermore preferred are a hydrogen atom, a benzene ring formed by $R^{A1}$ and $R^{A2}$ $R^{A3}$ and $R^{A4}$, or $R^{A5}$ and $R^{A6}$, alkyl groups and alkylthio groups.

Each of $R^1$ to $R^{12}$ and $R^{A1}$ to $R^{A6}$ may further have a substituent group, and examples thereof may be the same as those of $R^1$ to $R^{12}$ and $R^{A1}$ to $R^{A6}$. Each of $R^1$ to $R^{12}$ and $R^{A1}$ to $R^{A6}$ may have a ring structure, which may be condensed.

A preferred example of the compound of the present invention represented by the general formula (I) is represented by the general formula (II).

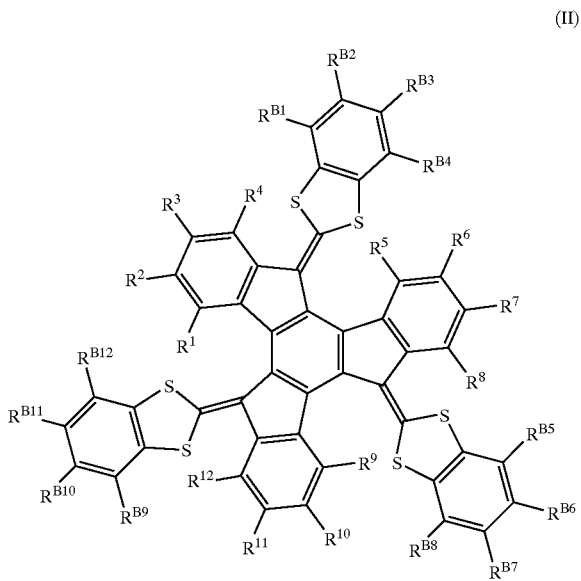

(II)

$R^1$ to $R^{12}$ in the general formula (II) are the same as those in the general formula (I). Each of $R^{B1}$ to $R^{B12}$ represents a hydrogen atom or a substituent group, with examples the same as those of $R^1$ to $R^{12}$ and $R^{A1}$ to $R^{A6}$. Each of $R^{B1}$ to $R^{B12}$ is preferably a hydrogen atom or an alkyl group, particularly a hydrogen atom.

Specific examples of the compound of the present invention represented by the general formula (I) or (II) will be illustrated below without intention of restriction.

Compound 1
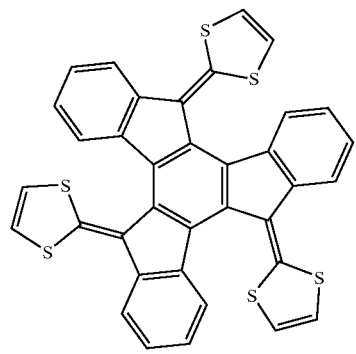
Compound 2
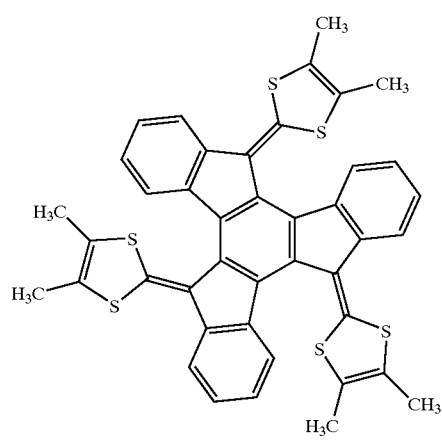
Compound 3
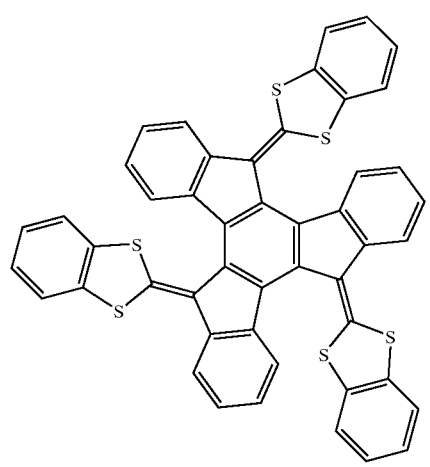
Compound 4
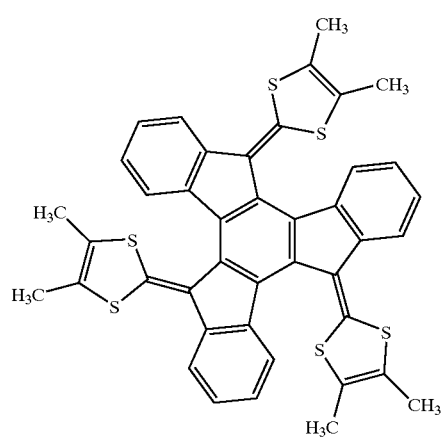
Compound 5
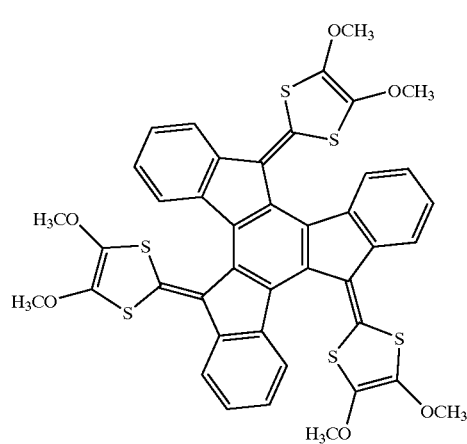
Compound 6
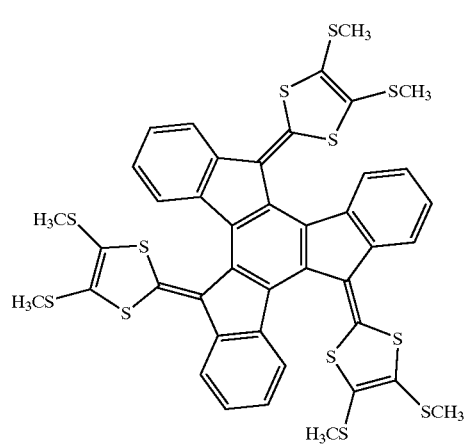

-continued
Compund 7
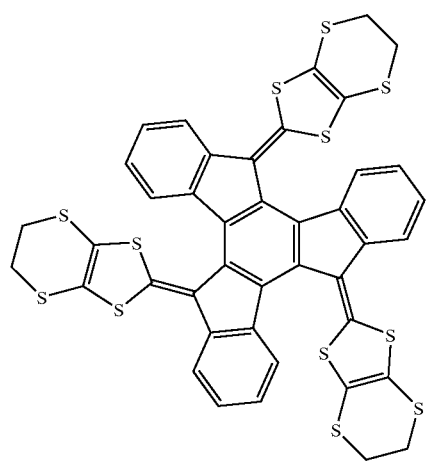
Compound 8
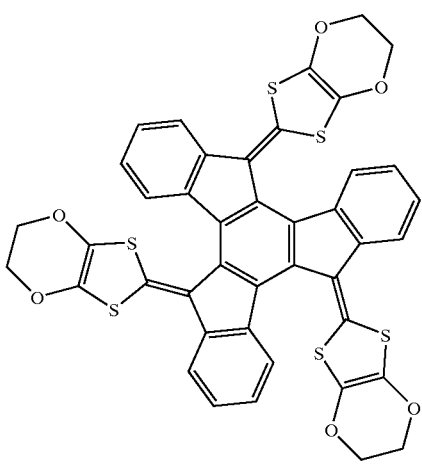
Compound 9
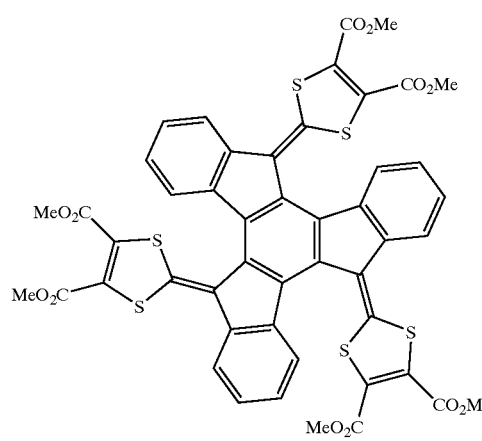
Compound 10
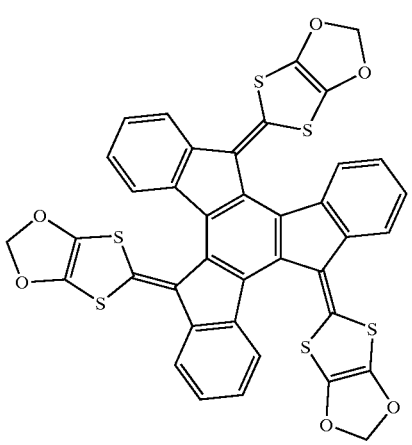
Compound 11
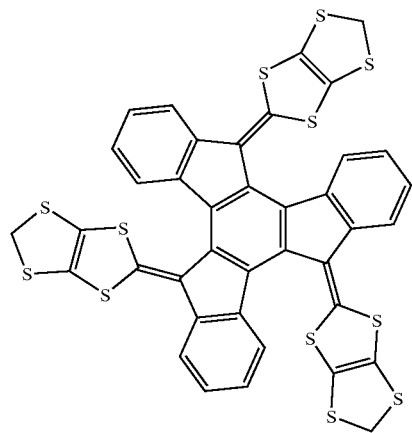
Compound 12
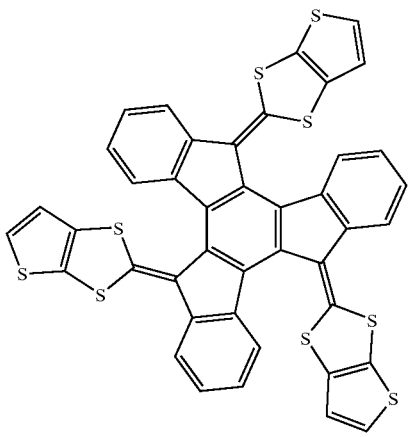

-continued
Compound 13
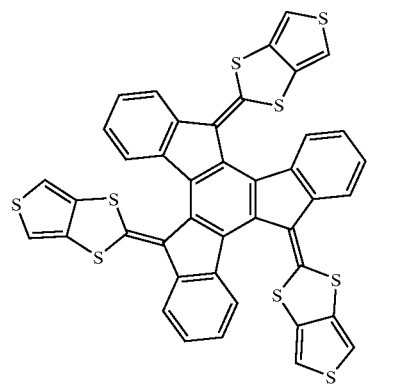
Compound 14
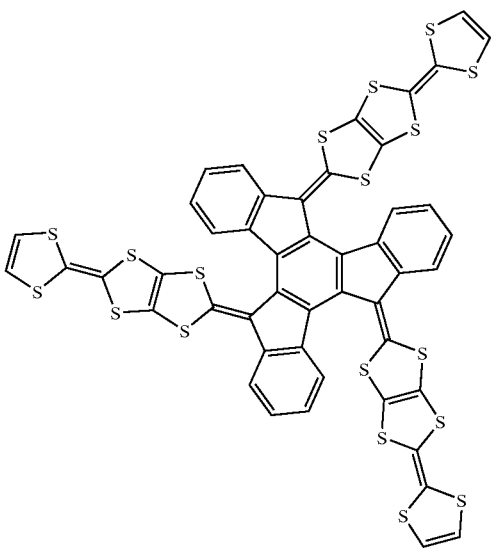
Compound 15
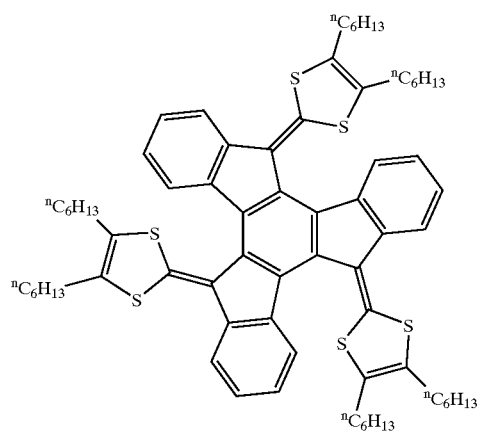
Compound 16
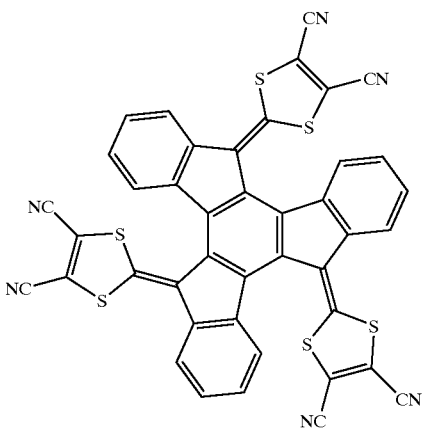
Compound 17
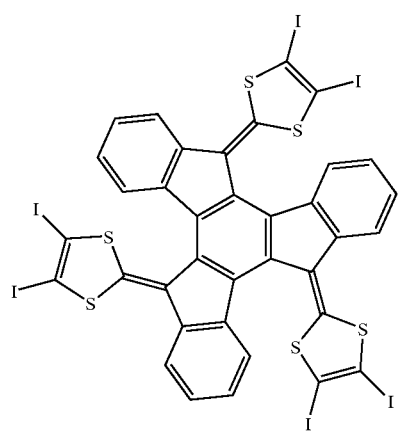
Compound 18
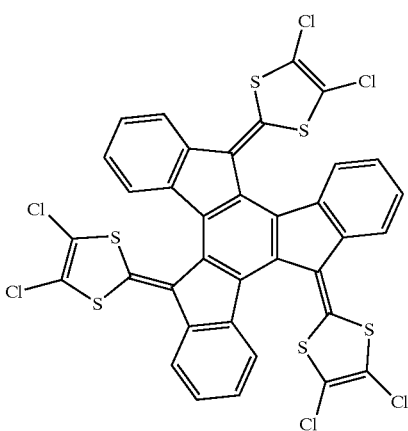

Compound 19
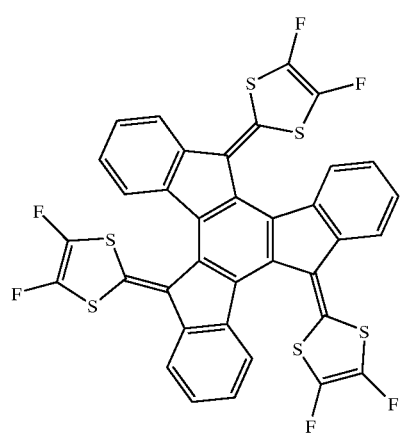
Compound 20
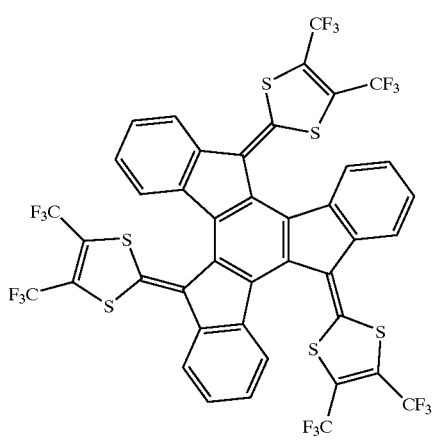
Compound 21
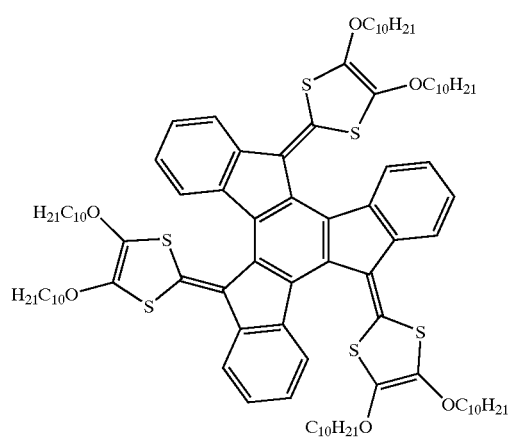
Compound 22
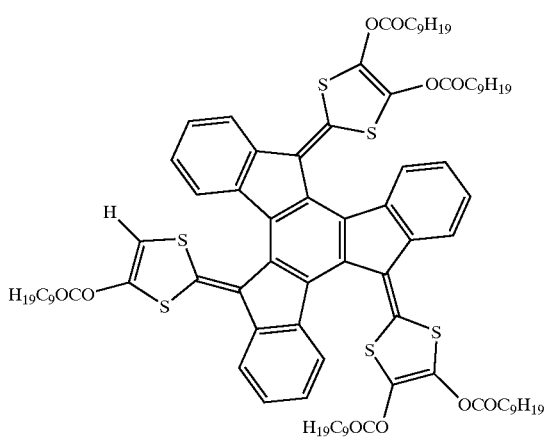
Compound 23
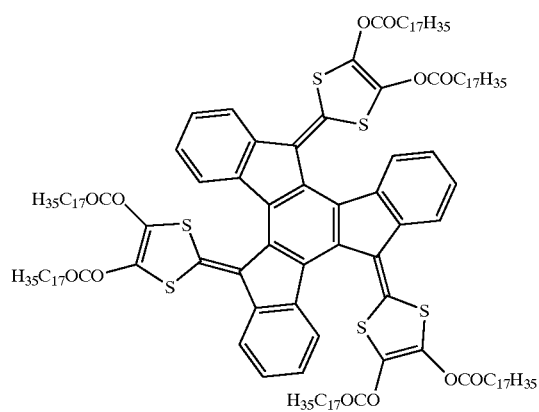
Compound 24
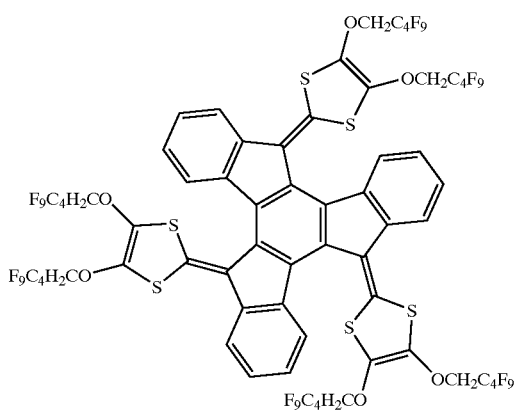

-continued
Compound 25
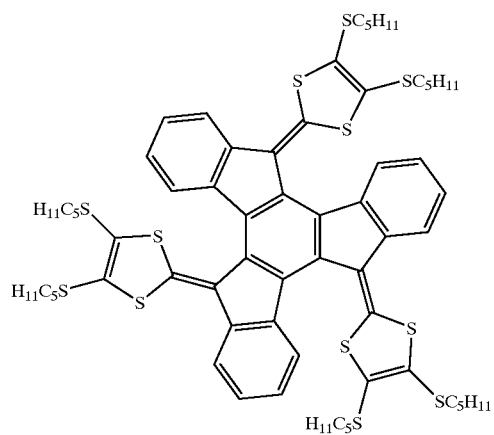
Compound 26
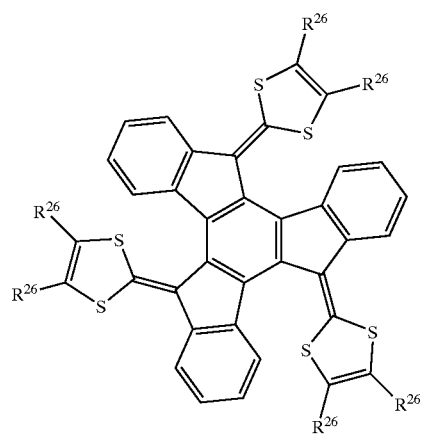
$R^{26} = -O-\overset{\overset{\displaystyle O}{\|}}{C}-CH_2-\overset{*}{\underset{H}{\overset{CH_3}{C}}}-C_6H_{13}$
*: Chiral carbon atom
Compound 27
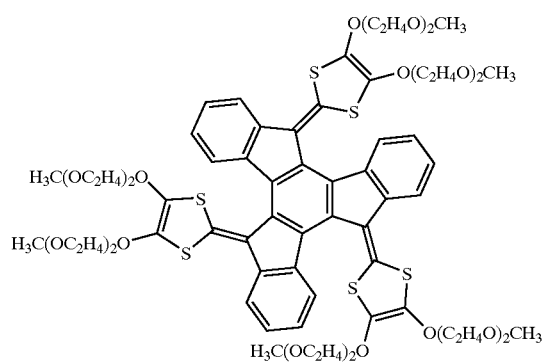
Compound 28
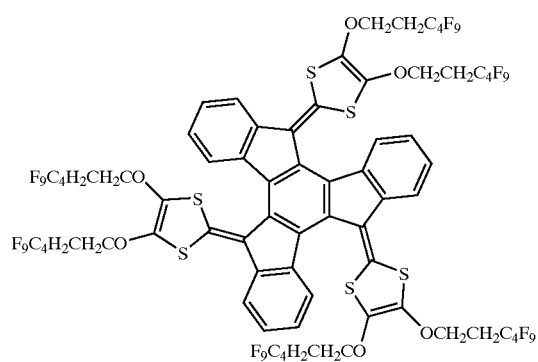
Compound 29
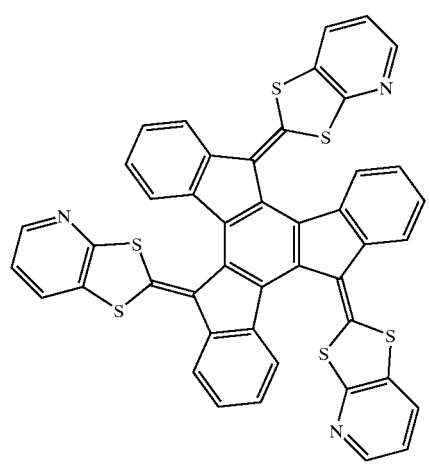
Compound 30
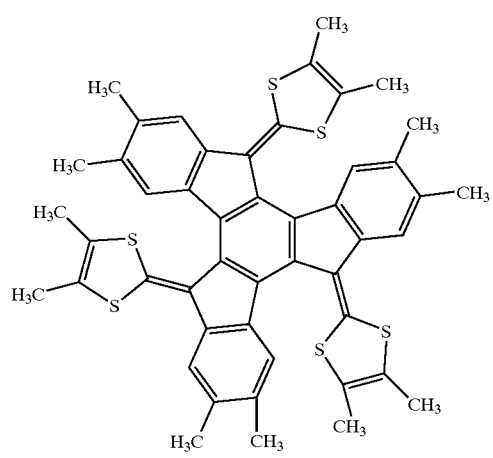

-continued
Compound 31
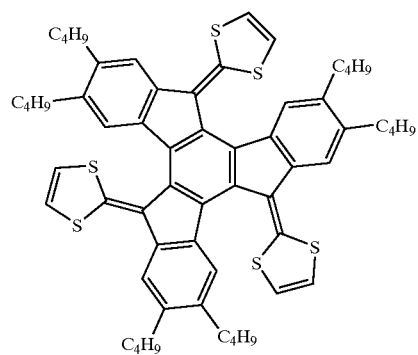
Compound 32
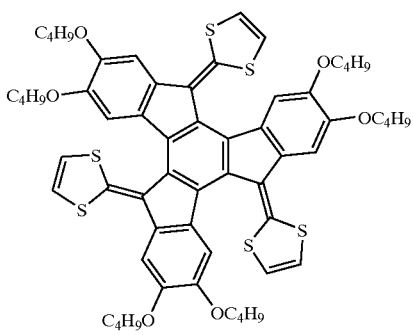
Compound 33
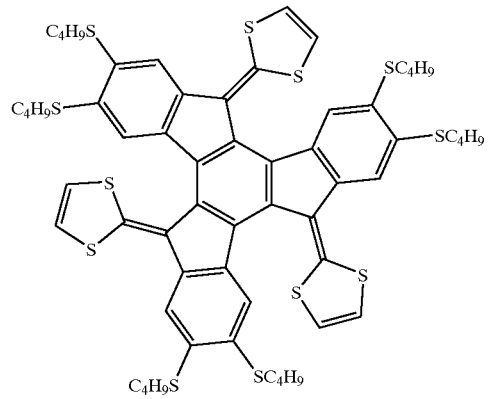
Compound 34
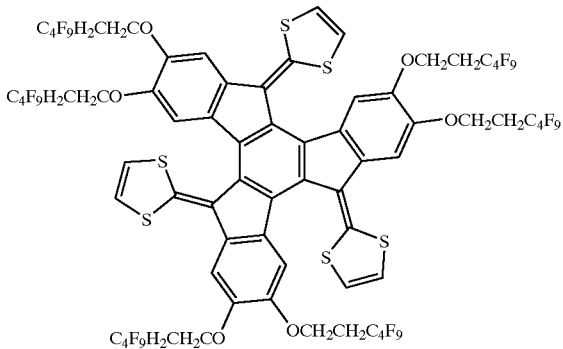
Compound 35
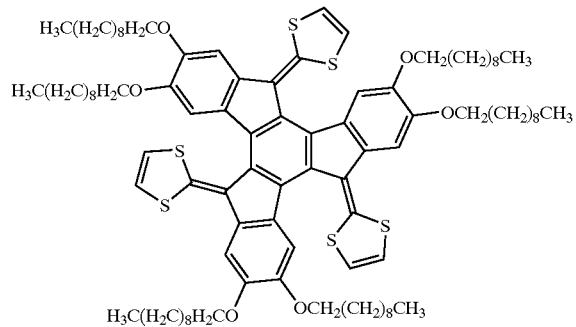
Compound 36
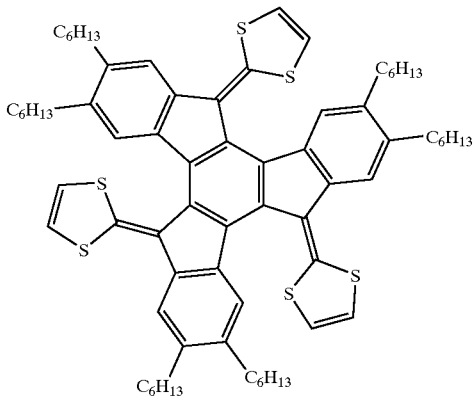

-continued

Compound 37

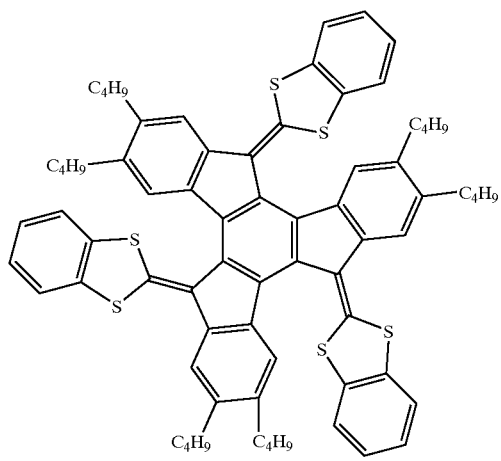

Compound 38

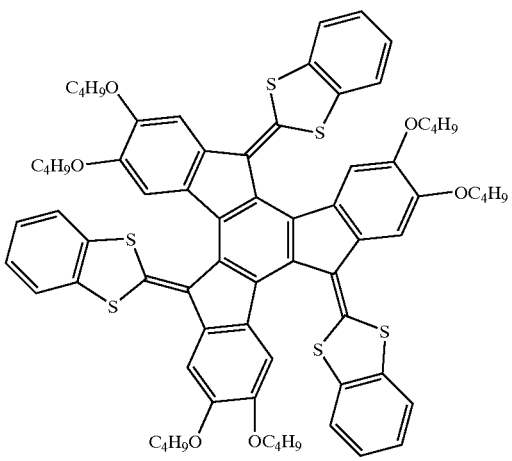

Compound 39

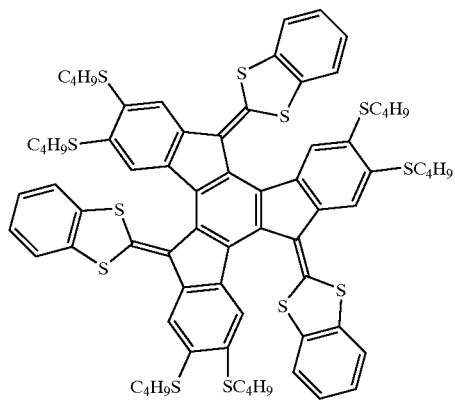

Compound 40

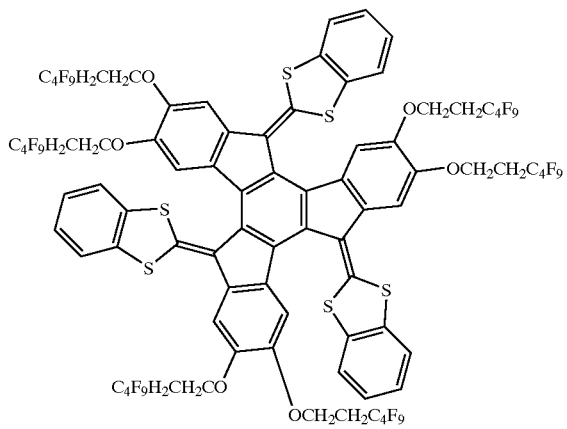

Compound 41

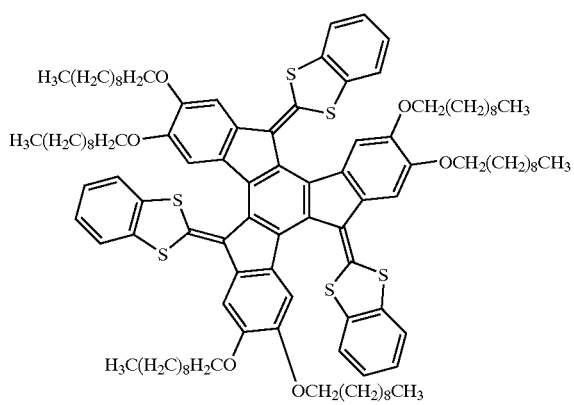

Compound 42

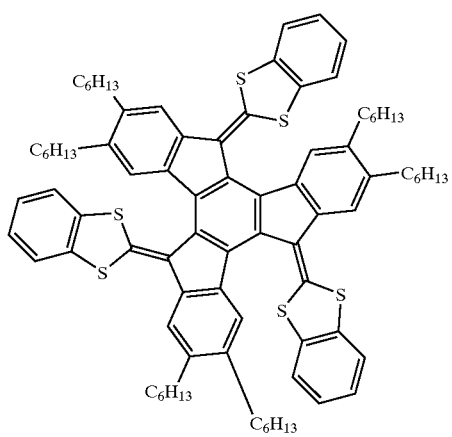

[2] Method for Synthesizing Sulfur-containing Compound

Though not particularly limited, the compound of the present invention represented by the general formula (I) or (II) is preferably synthesized by a coupling reaction between a truxene compound and a compound having a 1,3-dithiol ring skeleton because of easiness.

Preferred as the truxene compound is, for example, 1H-tribenzo[a,f,k]trindene-5,10-dihydro-5,10,15-trione having three carbonyl groups (truxenequinone). The truxene compound can be easily synthesized by such a method as self-condensation of indandione using a base (K. Jacob, et al., European Journal of Organic Chemistry, 2000, pp. 2047 to 2055), self-condensation of indandione using an acid (F. Sbrogio, et al, Synlett, 1994, pp. 761 to 762), etc. The temperature and time of the self-condensation reactions are not particularly limited and may be controlled according to the above references. The base may be added in amount of 1 to 2 equivalent to indandione, and the acid may be added in amount of 1 equivalent to large excess to indandione.

Preferred as the compound having a 1,3-dithiol ring skeleton are carbanions derived from phosphonium compounds represented by the general formula (III), carbanions derived from phosphonate compounds represented by the general formula (IV), and equivalents thereof. $R^{31}$ and $R^{32}$ in the general formula (III) and $R^{41}$ and $R^{42}$ in the general formula (IV) are the same as $R^{A1}$ to $R^{A6}$ in the general formula (I). Each of $R^{33}$ in the general formula (III) and $R^{43}$ in the general formula (IV) is not particularly limited but preferably an aryl group or an alkyl group having 1 to 20 carbon atoms, more preferably a phenyl group, a methyl group, an ethyl group or a butyl group.

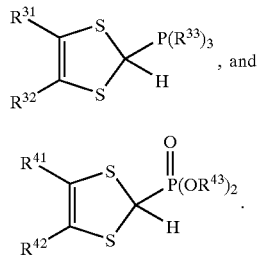

The carbanion or equivalent thereof derived from the compound of the general formula (III) or (IV) is subjected to the coupling reaction with the ketone. The coupling reaction is well known and disclosed in Ishikawa, Akiba and Inamoto, Tetrahedron Letters, 1976, No. 41, pp. 3695 to 3698, etc. For example, the carbanion may be prepared by the steps of dissolving the phosphonate compound of the general formula (IV) in tetrahydrofuran, cooling the resultant solution to −70° C. or lower, and adding an n-butyl lithium hexane solution to the cooled solution dropwise.

Truxenequinone in a state of solid or solution of tetrahydrofuran, etc. may be added to the carbanion solution and gradually heated to room temperature. The resultant mixture may be extracted with chloroform, etc. and purified by recrystallization, to obtain the compound of the present invention represented by the general formula (I) or (II) with a high purity.

[3] Light-emitting Device

The production method of the organic layer in a light-emitting device comprising the compound of the present invention is not particularly limited, and may be selected from a resistance-heating vapor deposition method, an electron beam method, a sputtering method, a molecular-stacking method, a coating method, an inkjet-printing method, a printing method, a transferring method, an electrophotography method, etc. Preferred among them are a resistance-heating vapor deposition method and a coating method because of good properties of the resultant light-emitting device and simplicity in process.

When the compound of the present invention is used as a light-emitting material, it may be used in any of a hole-injecting layer, a hole-transporting layer, an electron-injecting layer, an electron-transporting layer, a light-emitting layer, a hole-blocking layer and an electron-blocking layer, though it is preferably used in a hole-injecting layer or a hole-transporting layer.

In the case of using the compound of the present invention in a hole-injecting layer or a hole-transporting layer, the amount of the compound is preferably 10 to 100% by weight, more preferably 50 to 100% by weight, most preferably 80 to 100% by weight, particularly 100% by weight, based on the total weight of the layer comprising the compound. In the case of using the compound in the other layers, amount of the compound is preferably 5 to 90% by weight, more preferably 5 to 50% by weight, most preferably 5 to 30% by weight, based on the total weight of the layer comprising the compound. In any case, the compound of the present invention is uniformly dispersed in a polymer when these layers contain a polymer described below.

The light-emitting device of the present invention comprises a light-emitting layer or a plurality of organic layers including the light-emitting layer between a pair of electrodes, a positive electrode and a negative electrode. The light-emitting device of the present invention may comprise a hole-injecting layer, a hole-transporting layer, an electron-injecting layer, an electron-transporting layer, a hole-blocking layer, an electron-blocking layer, a protective layer, etc. in addition to the light-emitting layer. These layers may have other functions than their inherent functions.

(A) Electrodes

The positive electrode acts to supply holes to the hole-injecting layer, the hole-transporting layer, the light-emitting layer, etc. The positive electrode may be made of a metal, an alloy, a metal oxide, an electrically conductive compound, a mixture thereof, etc., and is preferably made of a material having a work function of 4.0 eV or more. Examples of the material for the positive electrode include electrically conductive metal oxides such as tin oxide, zinc oxide, indium oxide and indium tin oxide (ITO); metals such as gold, silver, chromium and nickel; mixtures and laminates of the electrically conductive metal oxides and the metals; electrically conductive inorganic compounds such as copper iodide and copper sulfide; electrically conductive organic compounds such as polyaniline, polythiophene and polypyrrole; mixtures and laminates of the electrically conductive organic compounds and ITO; etc. Preferable among them are the electrically conductive metal oxides, particularly ITO from the viewpoints of productivity, electroconductivity, transparency, etc.

Although the thickness of the positive electrode may be appropriately determined depending on the material used therefor, it is preferably 10 nm to 5 µm, more preferably 50 nm to 1 µm, further preferably 100 nm to 500 nm.

The positive electrode is generally formed on a substrate made of a soda lime glass, a non-alkali glass, a transparent resin, etc. The glass substrate is preferably made of a non-alkali glass to reduce ion elution. In the case of using the soda lime glass, a barrier coating of silica, etc. is preferably formed thereon beforehand. The thickness of the substrate is not particularly limited as long as it has sufficient mechanical strength. In the case of the glass substrate, the thickness thereof is generally 0.2 mm or more, preferably 0.7 mm or more.

A method for forming the positive electrode may be selected depending on the material used therefor. For example, the positive electrode made of ITO may be formed by an electron beam method, a sputtering method, a resistance-heating vapor deposition method, an ion plating method, a chemical reaction method such as a sol-gel method, a spraying method, a dipping method, a thermal CVD method, a plasma CVD method, a coating method using an ITO dispersion, etc.

To lower the driving voltage or to increase the light-emitting efficiency of the light-emitting device, the positive electrode may be subjected to a washing treatment, etc. For example, a UV-ozone treatment and a plasma treatment are effective in the case of the positive electrode of ITO.

The negative electrode acts to supply electrons to the electron-injecting layer, the electron-transporting layer, the light-emitting layer, etc. The material for the negative electrode may be selected from metals, alloys, metal oxides, electrically conductive compounds, mixtures thereof, etc. depending on ionization potential, stability, adhesion to a layer adjacent to the negative electrode such as the light-emitting layer. Examples of materials for the negative electrode include alkali metals such as Li, Na, K and Cs, and fluorides thereof; alkaline earth metals such as Mg and Ca, and fluorides thereof; gold; silver; lead; aluminum; alloys and mixtures of sodium and potassium; alloys and mixtures of lithium and aluminum; alloys and mixtures of magnesium and silver; rare earth metals such as indium and ytterbium; mixtures thereof; etc. The negative electrode is preferably made of a material having a work function of 4.0 eV or less, more preferably made of aluminum, an alloy or a mixture of lithium and aluminum, or an alloy or a mixture of magnesium and silver. In the mixtures of two metals such as lithium and aluminum, the component metals are mixed with each other without forming an alloy.

Although the thickness of the negative electrode may be appropriately determined depending on the material used therefor, it is preferably 10 nm to 5 μm, more preferably 50 nm to 1 μm, further preferably 100 nm to 1 μm.

The negative electrode may be formed by an electron beam method, a sputtering method, a resistance-heating vapor deposition method, a coating method, etc. A negative metal electrode may be formed by a metal deposition method, and a negative alloy electrode may be formed by simultaneously deposition of a plurality of metals or by deposition of an alloy.

The positive electrode and the negative electrode preferably have as low a sheet resistance as possible. Their sheet resistance is preferably a few hundred Ω/square or less.

(B) Light-emitting Layer

The light-emitting material for the light-emitting layer is not particularly limited as long as it has functions of receiving holes provided from the positive electrode, the hole-injecting layer, the hole-transporting layer, etc.; receiving electrons provided from the negative electrode, the electron-injecting layer, the electron-transporting layer, etc.; transporting charges; and emitting light by recombining holes and electrons when an electric field is applied to the light-emitting device. Examples of the light-emitting material include benzoxazole; benzoimidazole; benzothiazole; styrylbenzene; polyphenyl; diphenylbutadiene; tetraphenylbutadiene; naphthalimido; coumarin; perylene; perynone; oxadiazole; aldazine; pyralidine; cyclopentadiene; bis(styryl)anthracene; quinacridon; pyrrolopyridine; thiadiazolopyridine; styrylamine; aromatic dimethylidine compounds; 8-quinolinol derivative metal complexes; phenylpyridine derivative metal complexes; metal complexes such as organometallic complexes and rare-earth metal complexes; polymers such as polythiophene, polyphenylene and polyphenylenevinylene; the compound of the present invention; derivatives thereof; etc.

Though not particularly limited, the thickness of the light-emitting layer is preferably 1 nm to 5 μm, more preferably 5 nm to 1 μm, further preferably 10 nm to 500 nm.

Though not particularly limited, the light-emitting layer may be formed by a resistance-heating vapor deposition method; an electron beam method; a sputtering method; a molecular-stacking method; a coating method such as a spin-coating method, a casting method and a dip-coating method; an LB method; an ink-jet method; a printing method; a transferring method; an electrophotography method; etc. Preferable among them are the resistance-heating vapor deposition method and the coating method.

(C) Hole-injecting Layer and Hole-transporting Layer

The hole-injecting material and the hole-transporting material used for the hole-injecting layer and the hole-transporting layer are not particularly limited as long as they have a function of injecting holes provided from the positive electrode into the light-emitting layer, transporting holes, and/or blocking electrons provided from the negative electrode. Examples of the hole-injecting material and the hole-transporting material include the disc-like, sulfur-containing compounds of the present invention, carbazole, imidazole, triazole, oxazole, oxadiazole, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine, aromatic dimethylidyne compounds, porphyrin compounds, polysilane compounds, poly(N-vinylcarbazole), aniline copolymers, electrically conductive polymers and oligomers such as oligothiophenes and polythiophenes, derivatives thereof, etc.

Although the thickness of each of the hole-injecting layer and the hole-transporting layer may be appropriately determined depending on the material used therefor, it is preferably 1 nm to 5 μm, more preferably 5 nm to 1 μm, further preferably 10 nm to 500 nm. Each of the hole-injecting layer and the hole-transporting layer may have a single-layer structure of one or more materials, or a multi-layer structure having a plurality of layers made of the same or different materials.

The hole-injecting layer and the hole-transporting layer may be formed by a vacuum deposition method; an LB method; an ink-jet method; a printing method; a transferring method; an electrophotography method; a coating method using a solution or dispersion containing the above material such as a spin-coating method, a casting method and a dip-coating method; etc. A resin may be added to a solution or a dispersion used in the coating method. Examples of the resins include poly(vinyl chloride), polycarbonates, polystyrene, poly(methyl methacrylate), polyesters, polysulfones, poly(phenylene oxide), polybutadiene, poly(N-vinylcarbazole), hydrocarbon resins, ketone resins, phenoxy resins, polyamides, ethyl celluloses, poly(vinyl acetate), ABS resins, polyurethanes, melamine resins, unsaturated polyester resins, alkyd resins, epoxy resins, silicone resins, etc.

(D) Electron-injecting Layer and Electron-transporting Layer

The electron-injecting material and the electron-transporting material used for the electron-injecting layer and the electron-transporting layer are not particularly limited as long as they have a function of injecting electrons provided from the negative electrode into the light-emitting layer, transporting the electrons, and/or blocking holes provided from the positive electrode. Examples of the electron-injecting material and the electron-transporting material include triazole; triazine; oxazole; oxadiazole; fluorenone; anthraquinodimethane; anthrone; diphenylquinone; thiopyran dioxide; carbodimide; fluorenylidenemethane; distyrylpyrazine; anhydrides derived from a tetracarboxylic acid having such an aromatic ring as a naphthalene ring and a perylene ring; phthalocyanine; metal complexes such as 8-quinolinol derivative metal complexes, metallophthalocyanines and metal complexes containing a benzoxazole ligand or a benzothiazole ligand; the compound of the present invention; derivatives thereof; etc.

Though not particularly limited, the thickness of each of the electron-injecting layer and the electron-transporting layer is preferably 1 nm to 5 μm, more preferably 5 nm to 1 μm, further preferably 10 nm to 500 nm. Each of the electron-injecting layer and the electron-transporting layer may have a single-layer structure of one or more materials, or a multi-layer structure having a plurality of layers made of the same or different materials.

The electron-injecting layer and the electron-transporting layer may be formed by a vacuum deposition method; an LB method; an ink-jet method; a printing method; a transferring method; an electrophotography method; a coating method using a solution or a dispersion containing the above material such as a spin-coating method, a casting method and a dip-coating method; etc. The solution and the dispersion used in the coating method may comprise the same resin as in the hole-injecting layer and the hole-transporting layer.

(E) Protective Layer

The material used for the protective layer is not particularly limited as long as it has a function of shielding the light-emitting device from the penetration of moisture, oxygen, etc. that deteriorates the device. Examples of such materials include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; metal fluorides such as $MgF_2$, LiF, $AlF_3$ and $CaF_2$; polyethylene; polypropylene; polymethyl methacrylate; polyimides; polyureas; polytetrafluoroethylene; polychlorotrifluoroethylene; polydichlorodifluoroethylene; copolymers of chlorotrifluoroethylene and dichlorodifluoroethylene; copolymers of tetrafluoroethylene and at least one comonomer; fluorine-containing copolymers having main chains with cyclic structures; moisture-absorbing materials having a water absorption of 1% or more; moisture-resistant materials having a water absorption of 0.1% or less; etc.

Though not particularly limited, the protective layer may be formed by a vacuum deposition method, a sputtering method, an activated sputtering method, a molecular beam epitaxy method (MBE method), a cluster ion beam method, an ion-plating method, a plasma polymerization method, a high-frequency excitation ion-plating method, a plasma CVD method, a laser CVD method, a thermal CVD method, a gas source CVD method, a coating method, an ink-jet method, a printing method, a transferring method, an electrophotography method, etc.

The present invention will be described in more detail below with reference to Examples without intention of restricting the scope of the present invention.

EXAMPLE 1

Truxenequinone (Compound 2a) and Compound 2 illustrated below were synthesized according to the following scheme.

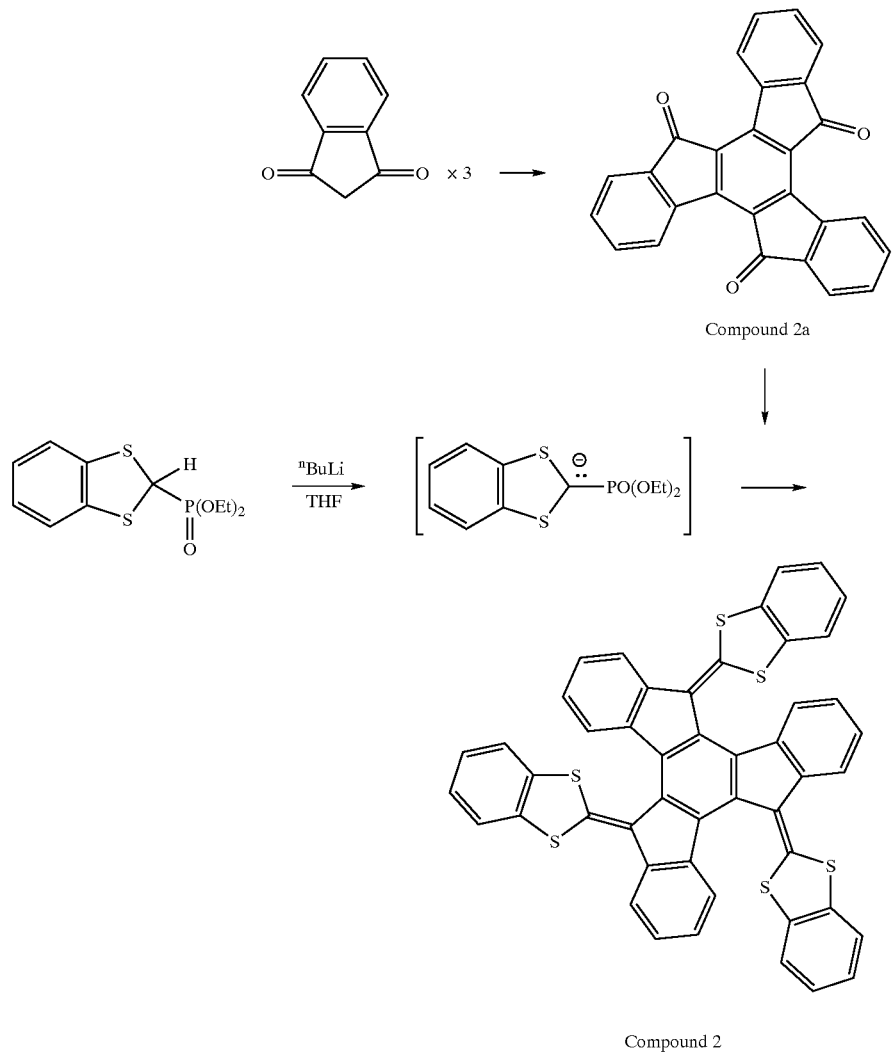

Compound 2a

Compound 2

1-1 Synthesis of Truxenequinone 4 g (27.4 mmol) of indandione and 6 ml of pyridine were introduced into a 200-ml, three-necked, round bottom flask and refluxed for 1 hour while heating. The resultant solution was cooled down to room temperature, and 50 ml of methanol was added thereto. The resultant mixture was stirred for a few minutes, and then filtrated under a reduced pressure to obtain yellowish brown powder on a filtering paper. The yellowish brown powder and a 10-% KOH methanol solution were introduced into a 100-ml, three-necked, round bottom flask, refluxed for 15 minutes while heating, and subjected to thermal filtering, to obtain brown powder on a filtering paper. The brown powder was purified by silica gel column chromatography (chloroform) to obtain 0.8 g (2.1 mmol) of truxenequinone (Compound 2a). The yield of truxenequinone was 27%.

1-2 Synthesis of Compound 2

After filling a 100-ml, three-necked, round bottom flask with a nitrogen gas, 581 mg (2.0 mmol) of 2-diethoxyphosphinyl-1,3-benzodithiol and 20 ml of dry THF were introduced thereinto and cooled down to −70° C. 1.44 ml (2.3 mmol) of an n-hexane solution of n-butyl lithium (1.6 M) was slowly added to the resulting mixture dropwise while stirring, and stirred at −70° C. for 10 minutes. 256 mg (0.67 mmol) of truxenequinone was added to this mixture at once, and gradually heated to room temperature. The resultant mixture was extracted with chloroform, washed with water two times, washed with a saturated aqueous sodium chloride solution and dried over magnesium sulfate. With solvents distilled off, the resultant brown powder was purified by recrystallization from chloroform/ethanol, to obtain 345 mg (0.44 mmol) of orange powder of Compound 2. The yield of Compound 2 was 65%.

Physical data of Compound 2 thus obtained were as follows: mp>300° C. (decomp.); $^1$H-NMR (300 MHz, CDCl$_3$), 7.05 (3H, dd, J=9.0, 7.4 Hz), 7.15 (6H, mc), 7.30 (3H, dd, J=9.0, 7.4 Hz), 7.41 (9H, mc), 7.88 (3H, d, J =7.5 Hz).

Comparative Example 1

A glass substrate of 25 mm×25 mm×0.7 mm having a 150-nm-thick ITO positive electrode available from Sanyo Vacuum Industries Co., Ltd. was subjected to etching and washing. N,N'-bis(1-naphthyl)-N,N'-diphenylbenzidine (NPD) of about 40 nm thick and tris(8-hydroxyquinolinato) aluminum (Alq) of about 60 nm thick were vapor-deposited in this order on the ITO positive electrode under the following conditions:

| Atmosphere: | vacuum at 10$^{-3}$ to 10$^{-4}$ Pa, |
| Deposition rate: | approximately 0.4 nm/second, and |
| Substrate: | at room temperature. |

With a patterned mask having a light-emitting area of 5 mm×5 mm placed on the resultant organic thin film in a deposition apparatus, magnesium and silver (mole ratio of magnesium/silver=10/1) were co-vapor-deposited thereon to a thickness of 250 nm, and silver was further vapor-deposited thereon to a thickness of 300 nm, to produce an EL device.

Constant DC voltage was applied to the EL device of Comparative Example 1 by "Source-Measure Unit 2400" available from Toyo Corporation to cause light emission, and the emitted light was measured with respect to luminance, emission wavelength and CIE chromaticity coordinates. The measurement of luminance by Luminance Meter BM-8 available from Topcon Corp. and emission wavelength and CIE chromaticity coordinates by Spectral Analyzer PMA-11 available from Hamamatsu Photonics K. K. revealed that the EL device of Comparative Example 1 emitted a green light with an emission wavelength of 535 nm, CIE chromaticity coordinates of (0.27, 0.63) and luminance of 7,500 cd/m$^2$ at voltage of 5 V. Second measurement after two weeks revealed that the luminance of the EL device of Comparative Example 1 was lowered to 1,420 cd/m$^2$.

EXAMPLE 2

An EL device was produced and measured with respect to luminance, emission wavelength and CIE chromaticity coordinates in the same manner as in Comparative Example 1 except for using Compound 2 in place of NPD. As a result, it was found that the EL device of Example 2 emitted a green light with an emission wavelength of 536 nm, CIE chromaticity coordinates of (0.27, 0.63) and luminance of 12,000 cd/m$^2$ at voltage of 3 V. Second measurement after two weeks revealed that the luminance of the EL device of Example 2 was still as high as 9,700 cd/M$^2$.

It was thus found that the light-emitting device of the present invention using the disc-like, sulfur-containing compound had such high durability that it was less deteriorated during storage or operation, and that it could be driven by a reduced voltage.

EXAMPLE 3

The same glass substrate having an ITO positive electrode as in Comparative Example 1 was subjected to etching and washing. The ITO positive electrode was spin-coated with a solution of 20 mg of polymethyl methacrylate (PMMA), 20 mg of Compound 2, 1 mg of a green-light-emitting material G-1 shown below, and 12 mg of 2-(4-biphenylyl)-5-(4-tert-butylphenyl)-1,3,4-oxadiazole (PBD) in 3 ml of dichloroethane. An organic thin film formed on the ITO positive electrode had a thickness of approximately 120 nm. With a patterned mask having a light-emitting area of 5 mm×5 mm placed on the organic thin film in a deposition apparatus, magnesium and silver (mole ratio of magnesium/silver=10/1) were co-vapor-deposited thereon to a thickness of 250 nm, and silver was further vapor-deposited thereon to a thickness of 300 nm, to produce an EL device.

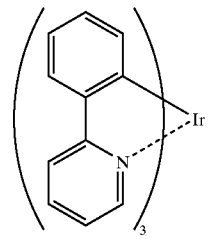

Green light-emitting material G-1

The EL device of Example 3 was measured in the same manner as in Comparative Example 1. As a result, it was found that the EL device of Example 3 emitted a green light with an emission wavelength of 520 nm and luminance of 4,900 cd/m$^2$. Second measurement after two weeks revealed that the luminance of the EL device of Example 3 was still as high as 4,000 cd/m$^2$.

Comparative Example 2

An EL device was produced and measured in the same manner as Example 3 except for using NPD in place of Compound 2. As a result, it was found that the EL device of Comparative Example 2 emitted a green light with an emission wavelength of 521 nm and luminance of 2,500 cd/m$^2$. Second measurement after two weeks revealed that the luminance of the EL device of Comparative Example 2 was reduced to as low as 1, 100 cd/m$^2$.

As is clear from the above experimental results, the light-emitting device of the present invention is high in luminance and light-emitting efficiency with improved durability, even if it is produced by a coating method, which is generally considered to provide light-emitting devices poor in luminance and light-emitting efficiency.

As described in detail above, the light-emitting device comprising at least one organic layer containing the compound of the present invention is high in luminance and durability, and can be driven by a low driving voltage. Further, the light-emitting device of the present invention can be produced by a coating method with reduced production cost.

What is claimed is:

1. A compound represented by the formula (I):

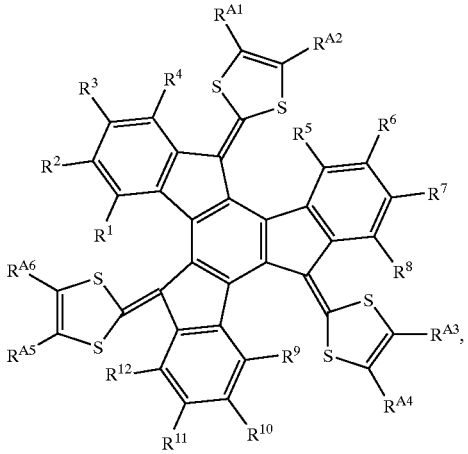

wherein each of to $R^1$ to $R^{12}$ and $R^{A1}$ to $R^{A6}$ represents a hydrogen atom or a substituent group, and adjacent groups of $R^1$ to $R^{12}$ and $R^{A1}$ to $R^{A6}$ may be bonded to each other to form a ring.

2. The compound of claim 1, wherein each of $R^1$, $R^4$, $R^5$, $R^8$, $R^9$ and $R^{12}$ is a hydrogen atom or an alkyl group.

3. The compound of claim 2, wherein each of $R^1$, $R^4$, $R^5$, $R^8$, $R^9$ and $R^{12}$ is a hydrogen atom.

4. The compound of claim 1, wherein each of $R^2$, $R^3$, $R^6$, $R^7$, $R^{10}$ and $R^{11}$ is a hydrogen atom, an alkyl group, an alkylthio group, an alkyloxy group, a cyano group, alkyloxy group or a halogen atom.

5. The compound of claim 4, wherein each of $R^2$, $R^3$, $R^6$, $R^7$, $R^{10}$ and $R^{11}$ is a hydrogen atom, an alkyl group or an alkylthio group.

6. The compound of claim 1, wherein each of $R^{A1}$ to $R^{A6}$ is a hydrogen atom, alkyl group, alkyloxy group, alkylthio group, a cyano group or halogen atoms.

7. The compound of claim 6, wherein each of $R^{A1}$ to $R^{A6}$ is a hydrogen atom, alkyl group or alkylthio group.

8. The compound of claim 1, wherein the compound represented by the formula (I) is a compound represented by the formula (II):

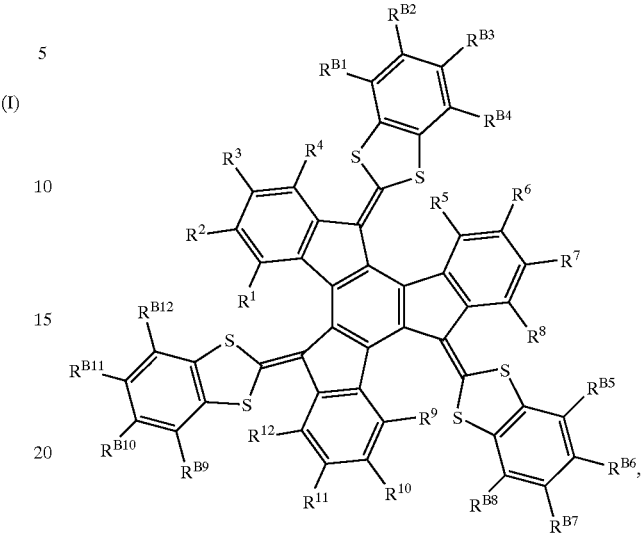

wherein each of $R^1$ to $R^{12}$ and $R^{B1}$ to $R^{B12}$ represents a hydrogen atom or a substituent group.

9. The compound of claim 8, wherein each of $R^{B1}$ to $R^{B12}$ is a hydrogen atom or an alkyl group.

10. A light-emitting device comprising a pair of electrodes and at least one organic layer comprising a light-emitting layer and disposed between said electrodes, wherein said at least one organic layer comprises the compound represented by the formula (I):

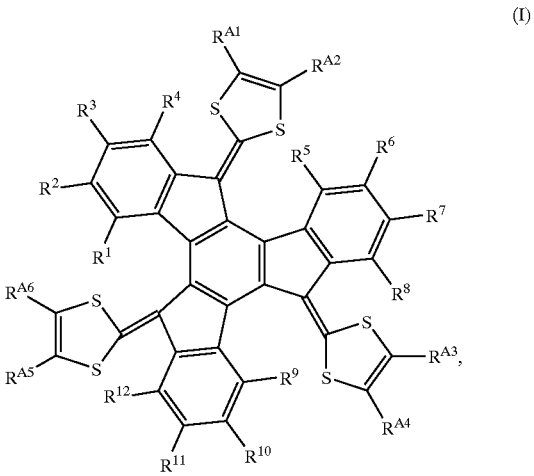

wherein each of $R^1$ to $R^{12}$ and $R^{A1}$ to $R^{A6}$ represents a hydrogen atom or a substituent group, and adjacent group of $R^1$ to $R^{12}$ and $R^{A1}$ to $R^{A6}$ may be bonded to each other to form a ring.

11. The light-emitting device of claim 10, wherein each of $R^1$, $R^4$, $R^5$, $R^8$, $R^9$ and $R^{12}$ is a hydrogen atom or an alkyl group.

12. The light-emitting device of claim 10, wherein each of $R^2$, $R^3$, $R^6$, $R^7$, $R^{10}$ and $R^{11}$ is a hydrogen atom, an alkyl group, an alkylthio group, an alkyloxy group, a cyano group, alkyloxy group or a halogen atom.

13. The light-emitting device of claim 10, wherein the compound represented by the formula (I) is a compound represented by the formula (II):

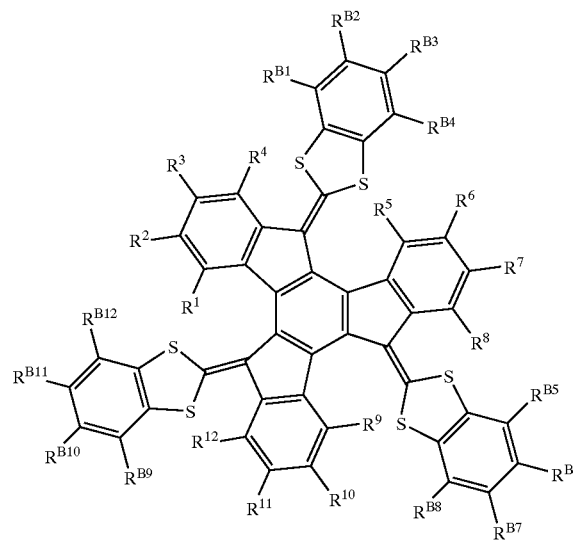

(II)

wherein each of $R^1$ to $R^{12}$ and $R^{B1}$ to $R^{B12}$ represents a hydrogen atom or a substituent group.

14. The light-emitting device of claim 13, wherein each of $R^{B1}$ to $R^{B12}$ is a hydrogen atom or an alkyl group.

15. The light-emitting device of claim 10, wherein said at least one organic layer further comprises a polymer.

16. The light-emitting device of claim 10, wherein said at least one organic layer is a hole-injecting layer or a hole-transporting layer.

17. The light-emitting device of claim 10, wherein the amount of the compound represented by the formula (I) in a hole-injecting layer or a hole-transporting layer is from 10 to 100% by weight.

18. The light-emitting device of claim 17, wherein the amount of the compound represented by the formula (I) in a hole-injecting layer or a hole-transporting layer is from 50 to 100% by weight.

19. The light-emitting device of claim 10, wherein the amount of the compound represented by the formula (I) in the other layers except a hole-injecting layer or a hole-transporting layer is from 5 to 90% by weight.

20. The light-emitting device of claim 19, wherein the amount of the compound represented by the formula (I) in the other layers except a hole-injecting layer or a hole-transporting layer is from 5 to 50% by weight.

* * * * *